United States Patent

Kureshy et al.

[11] Patent Number: 5,192,506
[45] Date of Patent: Mar. 9, 1993

[54] INCUBATOR PORT CLOSURE FOR AUTOMATED ASSAY SYSTEM

[75] Inventors: Fareed Kureshy; Charles A. DeAngelis, both of Westwood; Robert C. MacIndoe, Jr., Linwood, all of Mass.

[73] Assignee: P B Diagnostic Systems, Inc., Westwood, Mass.

[21] Appl. No.: 655,541

[22] Filed: Feb. 14, 1991

[51] Int. Cl.$^5$ .......................................... G01N 33/48
[52] U.S. Cl. ..................................... 422/64; 422/65; 422/67; 422/104; 436/45; 436/48; 435/809; 414/181; 414/292; 414/331; 221/198; 221/226
[58] Field of Search ...................... 422/63-65, 422/67, 104; 436/45, 47, 48; 435/809; 414/180, 181, 287, 292, 331; 221/198, 226

[56] References Cited

U.S. PATENT DOCUMENTS

| | | | |
|---|---|---|---|
| 4,219,529 | 8/1980 | Tersteeg et al. | 422/65 |
| 4,224,032 | 9/1980 | Glover et al. | 422/65 |
| 4,296,069 | 10/1981 | Smith et al. | 422/64 |
| 4,568,519 | 2/1986 | Hamilton et al. | 422/64 |
| 4,634,575 | 1/1987 | Kawakami et al. | 422/63 |
| 4,785,407 | 11/1988 | Sakagami | 422/67 |
| 4,908,320 | 3/1990 | Zakowski et al. | 436/45 |
| 5,061,446 | 10/1991 | Guigan | 422/64 |
| 5,075,079 | 12/1991 | Kerr et al. | 436/47 |

Primary Examiner—Lynn M. Kummert
Attorney, Agent, or Firm—Gaetano D. Maccarone

[57] ABSTRACT

An automated assay system includes a temperature controlled chamber with a conveyor therein. The conveyor carries berths past a port in a sidewall of the chamber to permit insertion and extraction of assay cartridges via the port into respective ones of the berths. An injector disposed outside the chamber and at the port includes a loader arm for advancing cartridges along a path through the port to accomplish insertion and extraction of a cartridge. A track is provided in the injector for guiding the assay module. A portion of the track connects by a swing arm to a pivot allowing the track portion to be swung away from the path for ejection of a cartridge. A door which provides for opening and closing of the port is connected to the swing arm to move concurrently with the swinging of the track portion. This allows for automatic closure of the port subsequent to an insertion or an extraction of a cartridge, and automatic opening of the port prior to insertion or extraction of the cartridge.

4 Claims, 10 Drawing Sheets

INCUBATOR PORT CLOSURE FOR AUTOMATED ASSAY SYSTEM

BACKGROUND OF THE INVENTION

This invention relates to an automated assay instrument and, more particularly, to an assembly for blocking a port in a wall of an incubator.

Various types of chemical tests are performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma, or serum may be tested to find evidence of disease, and to monitor therapeutic drug levels, by way of example. In the automated test instrument, samples of test fluids typically are provided in sample cups, and all of the process steps including pipetting of the sample onto an assay test element, incubation and readout of a test-result signal are performed automatically. The test instrument typically includes a series of work stations each of which performs a specific step in the test procedure. The assay element or cartridge is transported from one work station to the next by means of a conveyor, such as a carousel, to enable the test steps to be accomplished sequentially. The conveyor usually carries a plurality of the assay cartridges, each secured to a specific location on the upper surface of the conveyor. In the usual arrangement, the assay cartridges are spaced apart from each other in berths which are located along the periphery of the conveyor to facilitate automatic insertion and extraction.

In many automated instruments, a pipette head assembly is utilized in combination with disposable pipette tips which are used typically only once, and then discarded so as to eliminate a possible source of contamination of fluids, thereby to prevent errors in the assay results. In such systems, the pipette head assembly is required to pick up a disposable pipette tip, aspirate the appropriate fluid into the pipette tip, such as a sample fluid from a sample cup, and to dispense the required volume of fluid to the assay element. The fluid dispensing system in such instruments must meet various requirements which will be understood better from the following description of the typical manner in which a fluid dispensing assembly operates in an automated instrument.

In a typical construction of an automated instrument, the disposable pipette tips and the sample cups are arranged on carriers which are then placed on a carrier or tray supported by a movable table within the instrument. In one type of instrument, the pipette head assembly is transported horizontally (the X) direction and vertically (the Z direction), and the trays which hold the pipette tips and the sample cups are displaced from the front to the back of the instrument (the Y direction). The conveyor can be in the form of a carousel which carries the assay cartridges with rotational movement within an incubator. Initially, the pipette head assembly is driven downwardly to secure a disposable tip by frictional contact of a stem of the pipette head assembly with the interior of the disposable tip. Thereafter, a predetermined amount of fluid is aspirated into the pipette tip, and the tip is driven to a dispense position above an assay element where a predetermined volume of fluid is dispensed. Upon completion of the dispense step, the tip is discarded and a clean disposable tip secured to the stem of the pipette head assembly for the next dispense step.

One area of concern in the accurate conduction of automated assays is the maintenance of a carefully controlled temperature in the environment of the testing. Therefore, the assay cartridges are conveyed by a suitable conveyor, such as a rotating carousel, within a temperature controlled chamber such as an incubator. The chamber includes heaters which are controlled by automatic circuitry including sensors of the chamber temperature to maintain the predesignated temperature. Indeed, it is particularly advantageous to maintain both constancy of temperature and uniformity of temperature throughout the chamber. Such temperature control can be accomplished best if the chamber is completely sealed so as to prevent the development of currents of air flowing between the environment external to the chamber and the environment within the chamber.

A problem arises in that, in one construction of the temperature-controlled chamber an access port in the form of an elongated slot is placed in a top wall or roof of the chamber to permit insertion of a pipette for transference of liquid reagents between liquid-storage sites outside the chamber and a well within the cartridge, as well as for transference of liquid between a reservoir within the cartridge and a well in the cartridge. Furthermore, a port is provided in a sidewall of the chamber to enable a cartridge injector to insert assay cartridges onto the conveyor and to extract the cartridges when the assay is completed.

Both of these ports are generally open. The elongated slot in the top wall has a minimum width since only the pipette stem and the pipette tip have to pass through it. Thus, flow of air through this slot between the inside and the outside of the chamber is substantially impeded. The port in the sidewall for inserting and extracting the assay cartridges has considerably larger dimensions to accommodate the assay cartridges as well as the load-unload mechanism. Accordingly, it can permit sufficient air to flow between the inside and the outside of the chamber to cause undesirable variations in the chamber temperature. Therefore it would be desirable to have an assembly for blocking the port when assay cartridges are not being inserted into or extracted from the incubator.

SUMMARY OF THE INVENTION

These and other objects and advantages are provided by the invention for an automated assay system operative with assay cartridges. The system includes a temperature controlled chamber, the chamber having a sidewall with a port therein for insertion, of assay cartridges into and extraction of the cartridges from the chamber. A cartridge conveyor, such as a rotating carousel, is disposed within the chamber, and is provided with berths for holding the cartridges during analysis of fluid test samples by respective ones of the cartridges.

In accordance with the invention, a cartridge injector is disposed outside the chamber and at the port for inserting and extracting cartridges via the port. The injector includes a track and a loader arm which travels along the track, the loader arm engaging with a cartridge to move the cartridge along a predetermined path via the port into or out of the chamber. A portion of the track is connected via a swing arm to a pivot to enable a swinging of the track portion away from the path for dislodging a cartridge from the path, thereby to eject a spent cartridge.

An important feature of the invention is the inclusion in the system of a door, or shutter, which provides a closure of the port. A deflection of the door away from the port provides for an opening of the port. The door is connected to the swing arm so as to move concurrently with the swinging of the track portion. Thereby, an ejection of a cartridge automatically provides for a closure of the port. A returning of the track portion to the path via a swinging motion of the swing arm deflects the door away from the port for opening the port. Thereby, operation of the door can be synchronized with insertion and extraction of a cartridge so as to open the port prior to cartridge insertion or cartridge extraction, and to close the port subsequent to a cartridge insertion or a cartridge extraction.

BRIEF DESCRIPTION OF THE DRAWING

The aforementioned aspects and other features of the invention are explained in the following description, taken in connection with the accompanying drawing wherein:

FIGS. 10 and 11 present an enlarged fragmentary view of the system of FIG. 9 showing details in the construction of the injector, wherein FIG. 10 shows a cartridge in a loading position of the injector and FIG. 11 shows the cartridge in an eject position of the injector;

DETAILED DESCRIPTION

In order to explain the apparatus and operation of the invention to accomplish a closure of an incubator port of an automated assay system automatically with operation of an injector of cartridges into and out of the incubator, it is useful, first, to describe a suitable assay system employing some form of a conveyor, such as a carousel, with a fluid dispensing system for aspirating liquid reagents into disposable pipettes from sample cups or other reagent wells and delivering the liquids to an assay cartridge on the conveyor. Accordingly, the ensuing presentation begins with a description of the overall system, followed by a description of the process of the invention accomplishing closure of the port.

Figure 1:
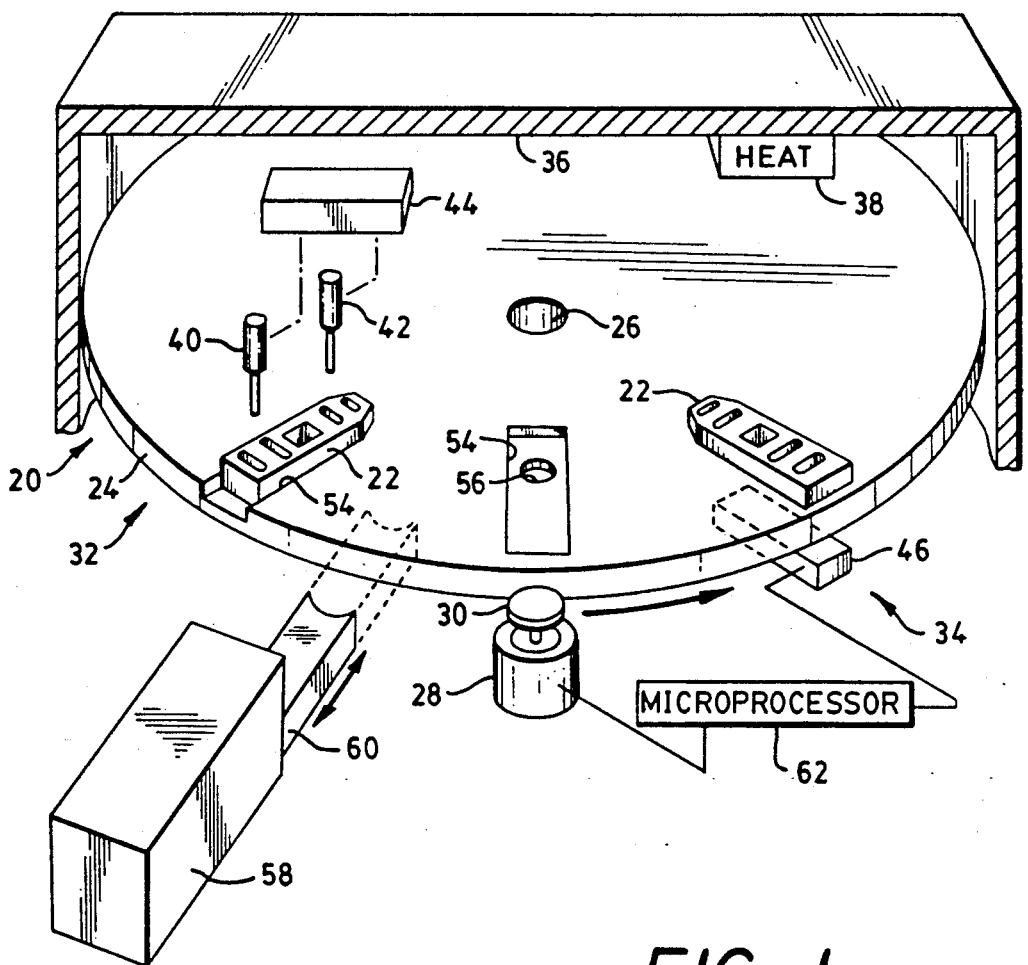
FIG. 1 is a stylized view, partially diagrammatic, of a test system employing assay cartridges, the system employing a carousel for moving the cartridges among various work stations.

In FIG. 1, a test system 20 provides automatically a sequence of chemical process steps to accomplish an assay of a test sample by cartridge 22. A plurality of cartridges 22 are employed within the system 20 to increase the throughput rate, one process step being provided with the contents of one cartridge concurrently with the performance of other process steps with the contents of other of the cartridges. The system 20 includes a turntable or carousel 24 which is rotated about an axle 26 by a motor 28. By way of example, the motor 28 may be mechanically coupled to the carousel 24 by a gear 30 or by a belt drive (not shown). The carousel 24 carries the cartridges 22 from one work station to another work station, two such work stations 32 and 34 being shown, by way of example, in FIG. 1. The carousel 24 rotates within an incubator 36. The incubator 36 has a heating system including a plurality of heaters represented diagrammatically by a heater 38 for maintaining a desired temperature at the various work stations. The maintenance of the desired temperature allows for a process step of incubation, this step being employed in an assay of analytes.

The work station 32 may employ one or more pipettes, two such pipettes 40 and 42 being shown by way of example, for delivering liquid to, and transferring liquid among, various chambers of a cartridge 22, as will be described hereinafter. The pipettes 40 and 42 are positioned and operated by a pipette mechanism 44 mechanically connected to the pipettes 40 and 42, as indicated by dashed lines. During the assay procedure, as a result of the reaction(s) and interaction(s) between the sample fluid and the test reagent(s) which take place, a detectable change is effected corresponding to the presence of an analyte or component of interest in the sample fluid. The detectable change may be a color change which may be read spectrophotometrically such as with densitometer or, in an assay method based on fluorescent-labeled biologically-active species or one which involves the generation of a fluorescent species as a result of a reaction between test reagents, a fluorescent output signal can be generated and read spectrofluorometrically. Such detectable changes may be read from above or below the assay module or cartridge 22. At work station 34, there is shown, by way of example, a fluorometer 46 for irradiating the reaction zone within the cartridge 22 and for measuring the fluorescence emitted from the fluorescent species present therein.

The carousel 24 may be arranged so as to accommodate varying numbers of cartridges 22. Each position, or berth 54, for holding a cartridge 22 is provided in this embodiment with a small aperture 56 to allow the radiating illumination to reach the reaction zone in the cartridge 22, and to permit the fluorescent emissions to be collected and measured. Also shown is an injector 58 for inserting a cartridge 22 in an empty berth 54, the injector 58 having a loader arm 60 for gripping a cartridge 22 during the insertion operation. The injector 58 also serves to extract a cartridge from a berth 54 by use of the arm 60 upon completion of a test procedure. Operation of the motor 28, the pipette mechanism 44, the fluorometer 46 and the injector 58 are synchronized by means of timing signals provided by a microprocessor 62.

Figure 2:
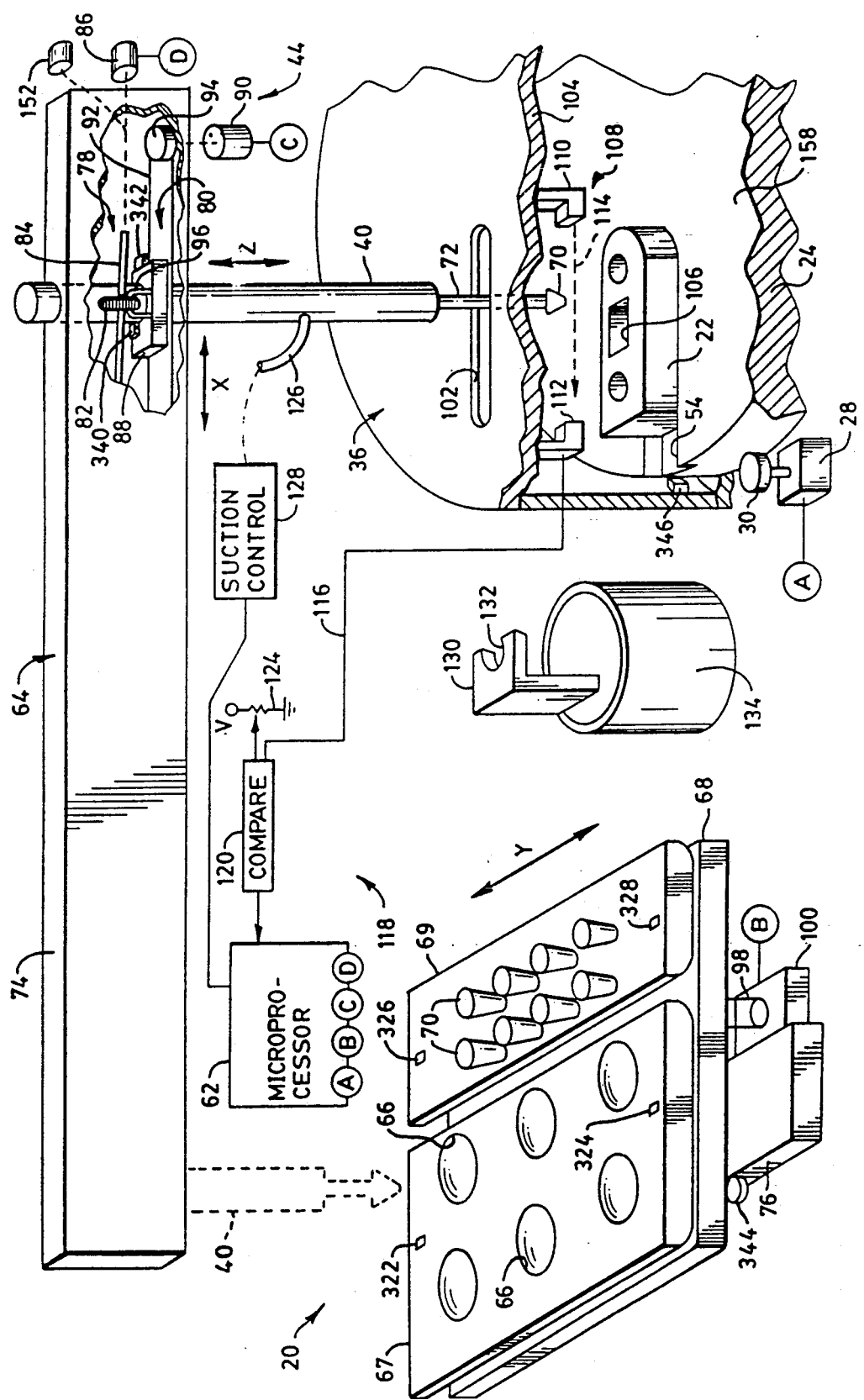
FIG. 2 is a stylized view, partially diagrammatic of a pipette transport for moving the pipette between a supply of tips, sample fluid reservoirs, and compartments of an assay cartridge, the figure showing also an optical detection system for sensing the location of a tip of the pipette.

FIG. 2 provides detail in the construction of the pipette mechanism 44 of FIG. 1. To facilitate description of the invention, the pipette mechanism 44 will be described hereinafter as having a pipette transport 64 operative with only one of the pipettes, namely, the pipette 40. The transport 64 provides for relative movement, in three dimensions, between the pipette 40 and a set of sample cups or reservoirs 66 located at a distance from the cartridge 22, the cups or reservoirs 66 serving to hold the fluid samples which are to be tested by the system 20. The reservoirs 66 are located on a tray 67 carried by a movable table 68 which also carries a tray 69 holding a set of tips 70 which are to be affixed to a stem 72 of the pipette 40. With reference to an X-Y-Z coordinate axes system, the pipette 40 is translatable in the X direction along a box beam 74 of the transport 64, and the table 68 is translatable in the Y direction by riding along a rail 76 of the transport 64. A vertical drive 78 is located within the beam 74 and serves to raise and to lower the pipette 40 in the Z direction. The X coordinate intercepts an axis of rotation of the carousel 24, and is therefore parallel to a radius of the carousel 24, and the Z coordinate is parallel to the axis of rotation of the carousel 24.

A horizontal drive 80 located within the box beam 74 drives the pipette in the X direction. The vertical drive 78 and the horizontal drive 80 are of conventional design, and are indicated in simplified fashion in FIG. 2. In simplified fashion, the vertical drive 78 may be described as comprising a wheel 82 slidably mounted to a spline shaft 84 which, alternatively, may have a square cross section. The shaft 84 is rotated by a motor 86. The horizontal drive 80 includes a base 88 which slides in the X direction along the beam 74 in response to rotation of a motor 90. The motor 90 drives a belt 92 through a pulley 94, the belt 92 being connected to the base 88 for translating the base 88 upon rotation of the pulley 94 by the motor 90. A fixture 96 upstanding from the base 88 slides the wheel 82 along the shaft 84 upon movement of the base 88 so that the wheel 82 stays in fixed position relative to the base 88. The pipette 40 passes through the base 88 so as to be translated in the X direction by the base 88. The wheel 82 is mechanically connected to the pipette 40, as by gear teeth on the wheel 82, or by means of a belt drive (not shown). The mechanical connection of the wheel 82 to the pipette 40 provides for a translation of the pipette 40 in the Z direction upon rotation of the wheel 82 by the motor 86. A belt drive 98 may be employed, similarly, for driving the table 68 in the Y direction in response to rotation of a motor 100 affixed to the rail 76.

As noted above in the description of the system of FIG. 1, the motor 28 is under control of the microprocessor 62. Similarly, the motors 100, 90, and 86 are also under control of the microprocessor 62. Connections of the motors 28, 100, 90, and 86 are indicated in FIG. 2 by terminals A, B, C, and D, respectively. Thereby, movement of the pipette 40 can be synchronized with a positioning of the cartridge 22 by the carousel 24 to a location directly beneath the beam 74. In order to provide access to the cartridge 22 by the pipette 44, a slot 102 is provided in a top wall 104 of the incubator 36. The slot 102 extends parallel to a radius of the carousel 24, and is parallel to the beam 74. The location of the slot 102 relative to the beam 74 permits the stem 72 of the pipette 40 to be lowered through the slot 102 selectively above a desired well or compartment of a plurality of compartments 106 of the cartridge 22. The length of the slot 102 is commensurate with the length of the cartridge 22 to permit displacement of the stem 72 in the X direction for alignment with a selected one of the compartments 106. The slot 102 is relatively narrow, and has a width large enough to clear the stem 72 and the tip 70 mounted on the distal end of the stem 72. With respect to the overall dimensions of the incubator 36, the area occupied by the slot 102 is sufficiently small to preclude any significant amount of air flow between the interior and the exterior of the incubator 36. Thereby, the slot 102 has no more than a negligible effect in the control of the incubator temperature, which temperature is controlled by the heater 38 (FIG. 1).

In an embodiment of an automated assay instrument, an optical detection system 108 is provided to signal the microprocessor 62 when the tip 70 of the pipette 40 has advanced in the downward direction to a predetermined distance from the selected compartment 106. The detection system 108 comprises a light source 110 which, by way of example, may be a semiconductor diode which emits infrared radiation. The detection system 108 also comprises a light detector 112, the light being indicated by a light beam 114. The detector 112, which may comprise a semiconductor photodiode, emits an electric current along line 116 in response to light of the beam 114 incident upon the detector 112.

The detection system 108 includes electrical comparison circuitry 118 for measuring the magnitude of the current on line 116. By way of example in the construction of the circuitry 118, the circuitry 118 comprises a comparator 120 and a resistive voltage divider 124 providing a reference voltage to the comparator 120. The divider 124 comprises a potentiometer for allowing manual adjustment of the reference voltage for initial alignment of the detection system 108. The divider 124 provides for selection of a comparator reference voltage in accordance with the degree of optical transparency of the tip 70.

In the operation of the detection system 108, the full strength of the light beam 114 is incident upon the detector 112 in the absence of the pipette 40. By way of example, the pinette 40 may be at the location of one of the reservoirs 66, as indicated in phantom view of the pipette. During maximum intensity of the received optical signal at the detector 112, a maximum current and voltage appear on line 116. During descent of the pipette 40, the tip 70 interrupts the light beam 114. The line 116 is connected to an input terminal of the comparator 120 which outputs a logic-1 signal to the microprocessor 62 under conditions of maximum illumination of the detector 112, as occurs prior interruption of the light beam 114 by the pipette 40. Interruption of the light beam 114 greatly reduces the intensity of light received at the detector 112 so that the comparator 120 outputs a logic-0 signal to the microprocessor 62. The extent of the interruption of the light depends on the degree of the transparency of the tip 70. The tip 70 is fabricated typically of a translucent polymeric material.

Liquid reagent is drawn into the pipette tip 70 by vacuum and expelled from the tip 70 by pressure delivered to the pipette 40 by a suction tube 126 under control of a suction control unit 128. The tube 126 is flexible and of sufficient length to connect the suction control unit 128 with the pipette 40 at all locations of the pipette 40. The control unit 128 is connected to the microprocessor 62 which commands the control unit 128 to apply vacuum for inducting liquid, and for releasing vacuum and applying positive pressure, if necessary, to expel the liquid reagent. Induction of liquid sample is done from a selected one of the reservoirs 66. Expelling of the liquid sample is accomplished only when the tip 70 is in the position for dispensing the liquid to the selected one of the compartments 106 in the designated cartridge 22. It is noted also that induction of liquid reagent can be accomplished at one of the compartments 106 of the cartridge 22 to be dispensed in another of the compartments 106. In this respect, a reservoir for storage of liquid reagent can be located directly within the cartridge 22. The location of the various reservoirs 66 of the table 68 is stored in a memory of the microprocessor 62. This enables the microprocessor 62 to move the table 68 to a specific address in the Y direction, and to move the pipette 40 to a specific address in the X direction, the X and the Y components of the address fully identifying the requisite one of the reservoirs 66. In similar fashion, the microprocessor 62 stores locations of the available tips 70 held by the table 68 so that successive ones of the tips 70 can be selected for affixation to the stem 72.

The transport 64 is operative in the process of affixing a tip 70 to the stem 72 of a pipette 40, and in the detachment of the tip 70 from the stem 72. The procedure begins by a lifting of the pipette 40 so that the tip 70 clears the slot 102. The pipette 40 is then free to move along the beam 74 to an extractor 130. The extractor 130 has a semicircular channel 132 cut out in the edge of a horizontal portion of the extractor 130, the channel 132 having a diameter large enough to permit clearance of the stem 72 by the channel 132, but small enough to permit engagement of the channel 132 with the tip 70. Under commands of the microprocessor 62, the pipette is brought towards the extractor 130 with the tip 70 being below the channel 132. The stem 72 enters the channel 132 after which the pipette 40 is raised to engage the tip 70 with the extractor 130. The tip 70 remains stationary as the stem 72 lifts out of the tip 70. Thereupon, the tip 70 falls into a bin 134 for collection of used tips 70. It is advisable to employ the extractor 130 at the beginning of operation of the test system 20 to ensure that the stem 72 is free for reception of a new tip 70.

After ensuring that the stem 72 is free for reception of a tip 70, the pipette 40 is brought, by displacement in the X direction, to a location above the table 68, whereupon the table 68 is translated in the Y direction to bring the stem 72 above and in registration with a selected tip 70 held by the table 68. The pipette 40 then advances downward to make frictional contact with the interior surface of the tip 70. Thereupon, the pipette is raised, and the tip is retained on the distal end of the stem 72 by friction forces.

Figure 3:
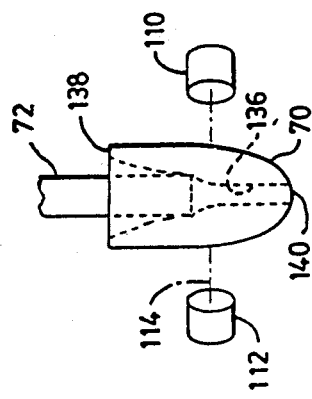
FIG. 3 is an enlarged fragmentary view of a tip of the pipette within a light beam of the optical detection system.

With reference also to FIG. 3, the distal end of the stem 72 is shown making frictional contact with the surface of an internal channel 136 of the tip 70. The channel 136 extends along a central longitudinal axis of the tip 70 from one end of the tip to the opposite end of the tip. The channel 136 has a circular cross-sectional shape of varying diameter, the diameter being larger at the top end 138 than at the bottom end 140. As the stem 72 advances downwardly into the channel 136, constriction of the channel 136 produces frictional forces which tighten the tip 70 upon the stem 72. These frictional forces are sufficient to ensure a secure attachment of the tip 70 to the stem 72 during transfer of liquid reagent during test procedures of the system 20. However, the frictional forces are sufficiently small to permit the extractor 130 to slide the tip 70 off of the stem 72 upon completion of a transfer of liquid reagent.

With respect to the operation of the system 20, it is noted that the manner of affixing the stem 72 to the tip 70 provides substantial uniformity in the locations of successive tips 70 upon the stem 72. However, in view of the flexibility of the plastic material of the tip 70 brought about by contact with the relatively rigid tube of the stem 72, and in view of some variation in frictional forces among the tips 70, it has been found that there is slight variation among the locations of the bottom ends 140 of the tips 70 relative to the distal end of the stem 72. This variation is sufficient to serve as a source of inaccuracy to the dispensing of liquid in the compartments 106 of the cartridge 22. The system automatically corrects for these variations in tip location by sensing the location of the bottom end 140 of the tip 70 by means of the light beam 114. The procedure for correcting for the variations in tip location is explained further with reference to the diagram of FIG. 4 and the flow charts of FIGS. 5-6.

Figure 4:
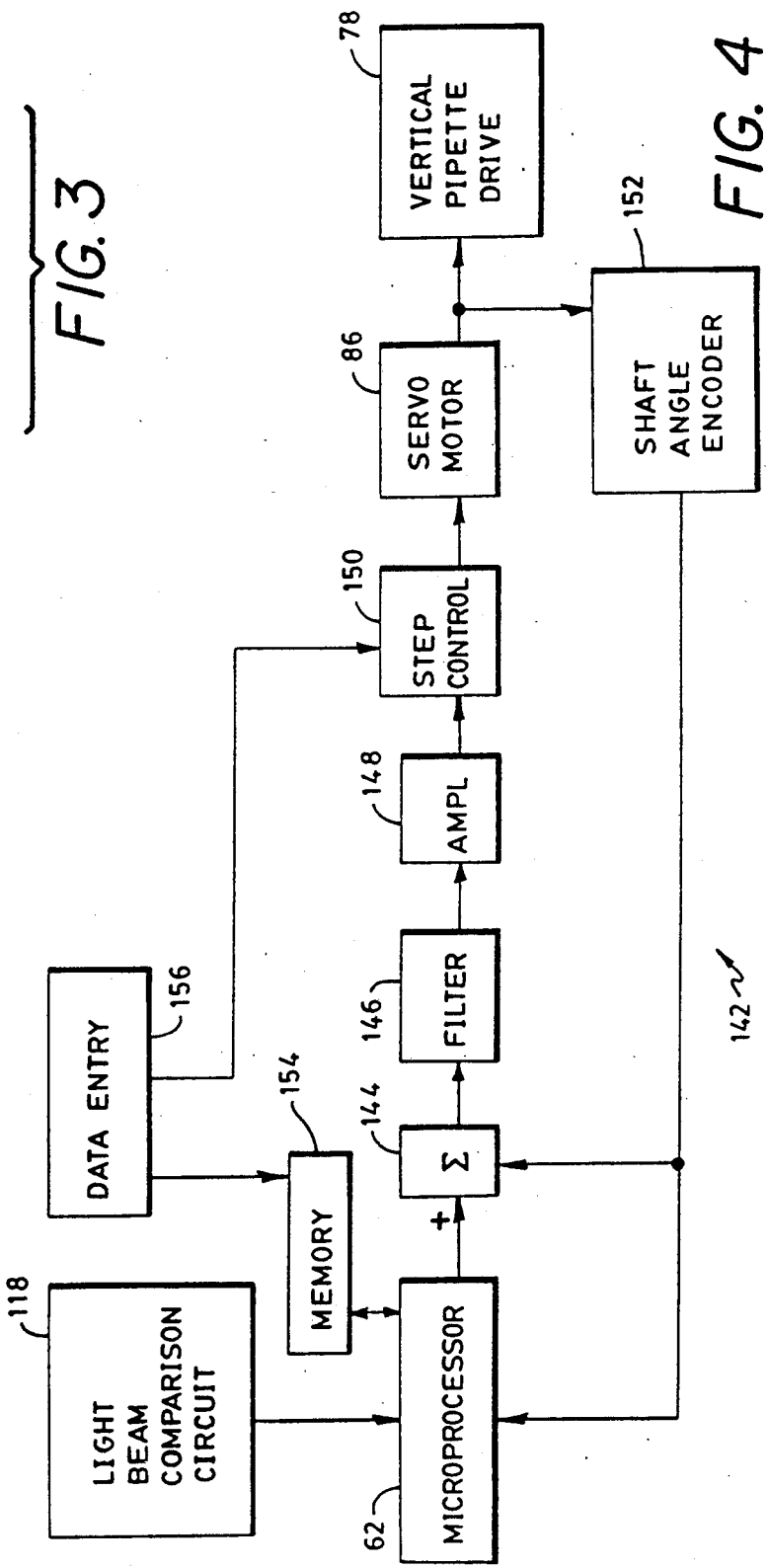
FIG. 4 is a block diagram showing a servo control loop of the pipette transport operative with a microprocessor for positioning the pipette within the vertical direction.

FIG. 4 shows a feedback circuit 142 for interconnecting the microprocessor 62 with the motor 86 for operation of the vertical pipette drive 78 disclosed in FIG. 2. As shown in FIG. 4, the circuit 142 includes a summer 144, a filter 146, an amplifier 148, a stepping motor controller 150, a shaft angle encoder 152 (also shown in FIG. 2), a memory 154 of the microprocessor 62, and an entry device 156, such as a keyboard, for entering data into the memory 154. In a preferred embodiment, all of the motors 28, 100, 90 and 86 are constructed as stepping motors.

In operation, for lowering the pipette 40 towards the cartridge 22 (FIG. 2), the microprocessor 62 successively enters new locations on the path of travel of the pipette 40 in the Z direction. Location signals of the microprocessor 62 are applied to one input terminal of the summer 144. The present location of the tip 70, as estimated by the encoder 152 is applied to a second input terminal of the summer 144 to be subtracted from the value input at the first terminal of the summer 144. It is noted that the encoder 152 provides an accurate value of the location of the pipette stem 72, but not of the tip 70, because the position of the tip 70 relative to the stem 72 varies from tip to tip because of the frictional fit explained above. Therefore, a value of shaft angle outputted by the encoder 152 can be taken only as an estimate of the true position of the tip 70.

The signals outputted by the encoder 152 and by the microprocessor 62 are formatted digitally. The summer 144 forms the difference of these two signals and applies the difference as the loop error signal to be filtered by the filter 146. In accordance with the usual practice in the construction of the feedback loops, the filter 146 may be a low-pass filter, and may include a lead-lag filter component. The filter 146 provides stability to the feedback loop. An output signal of the filter 146 is amplified by the amplifier 150, and is applied via the controller 150 to the stepping motor 86. The loop gain and bandwidth, as established by the amplifier 150 and the filter 146, in conjunction with the motor 86 determine the dynamic response of the loop in a manner well known in the design of servomechanisms. The motor 86 rotates towards the rotational position commanded by the microprocessor 62. As the motor 86 rotates, the vertical drive 78 lowers the pipette 40. By way of alternative embodiment in the construction of the feedback circuit of FIG. 4, it is noted that the functions of the summer 144 and the filter 146 can be accomplished directly within the microprocessor 62 by suitable programming of the microprocessor 62. In such a case, the microprocessor 62 outputs the error signal directly to the amplifier 148 for driving the motor 86.

With respect to the circuit shown in FIG. 4, the microprocessor 62 continues to input further values of position along the path traveled by the pipette 40 until the light-beam comparison circuit 118 signals the microprocessor 62 of a break in the light beam. The location of the tip 70 is now known accurately by virtue of contact of the tip 70 with the light beam 114. The pipette 40 now travels through an additional distance to bring the tip 70 into the dispensing position relative to the cartridge 22. The value of the additional distance of positional travel is based on data stored in the memory 154. The microprocessor 62 reads the memory 154 to obtain the travel data. A person calibrating the test system 20 provides the requisite data on additional travel based on a knowledge of a reference point which, in a preferred embodiment is the height of the cartridge 22 relative to a top surface 158 of the carousel 24. This height data is entered via the entry device 156 to the memory 154. By way of example, the entry device 156 may be constructed as a touch panel located at a position of convenience to an operator of the system 20.

Figure 6:
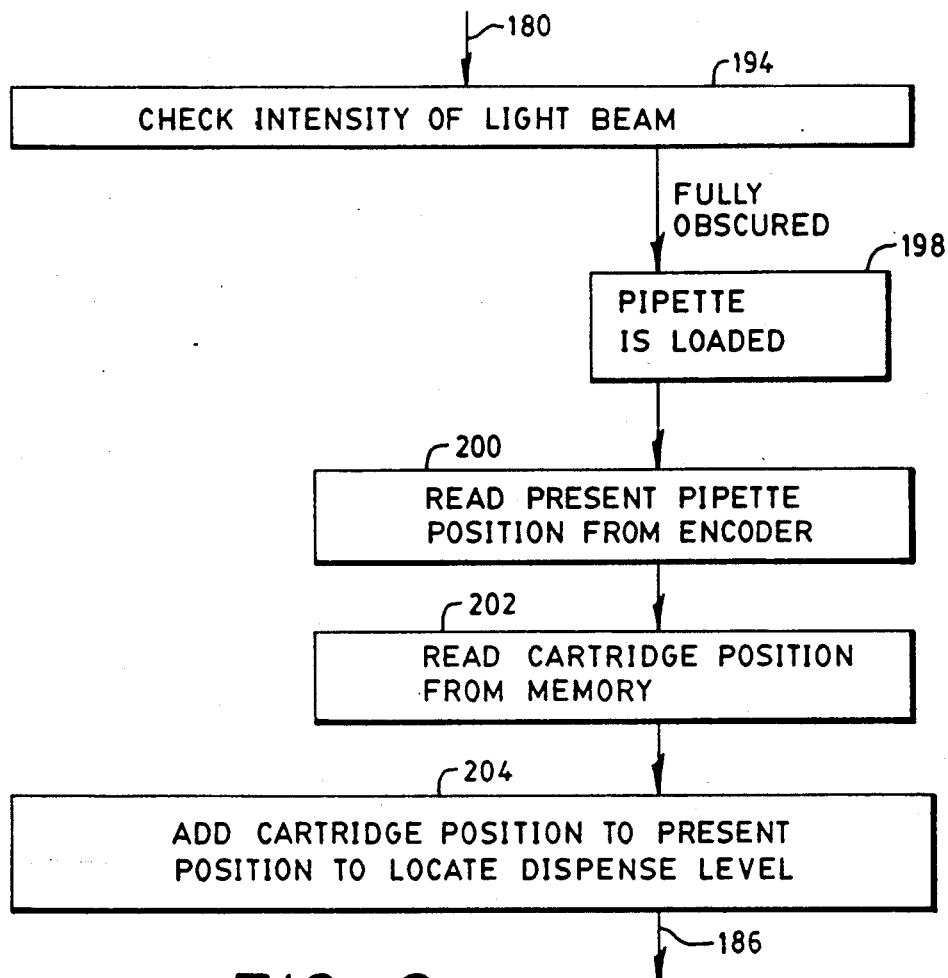
FIG. 6 shows details in a block of the chart of FIG. 5 relating to the computation of additional pipette travel.
Figure 7:
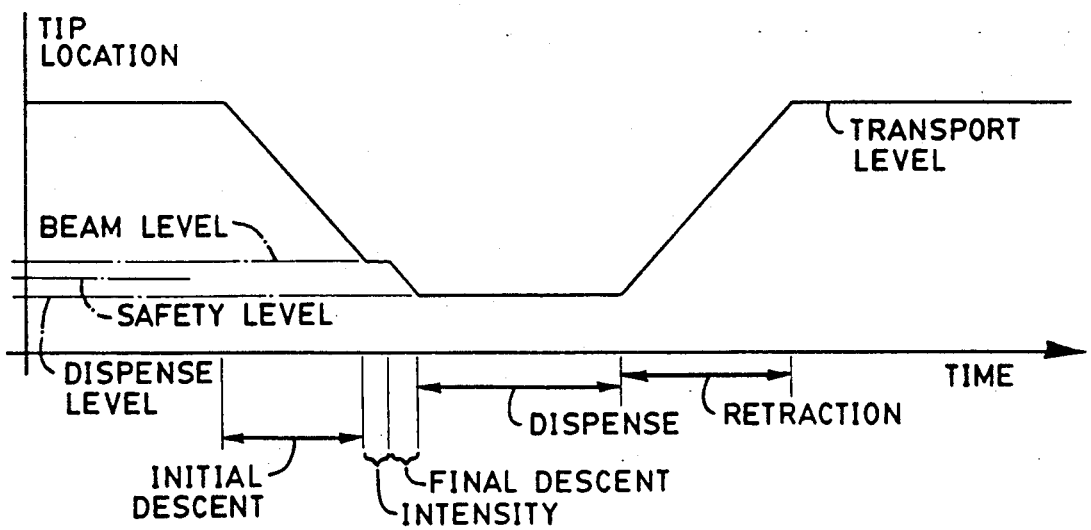
FIG. 7 is a timing diagram showing vertical movement of the pipette.

The operation of the feedback circuit 142 may be explained further with reference to FIG. 2 and with reference to the timing diagram of FIG. 7. Prior to the lowering of the pipette 40, the tip 70 is at a sufficiently high elevation to permit transporting the pipette 40 in the X direction between the carousel 24 and the table 68. This is referred to in FIG. 7 as the transport level. The pipette 40 then undergoes its initial descent during an interval of time identified in FIG. 7. The initial descent interval ends with the breaking of the light beam 114. Thereupon, there is the final interval of descent in which the pipette 40 descends the additional travel. This brings the pipette tip to the dispense level indicated in FIG. 7. After completion of a dispensing interval of time, the feedback circuit 142 raises the pipette 40 back to the transport level during a retraction interval shown in FIG. 7. Also shown in FIG. 7 is a safety level which will be described with reference to the flow charts of FIGS. 5-6.

Figure 5:
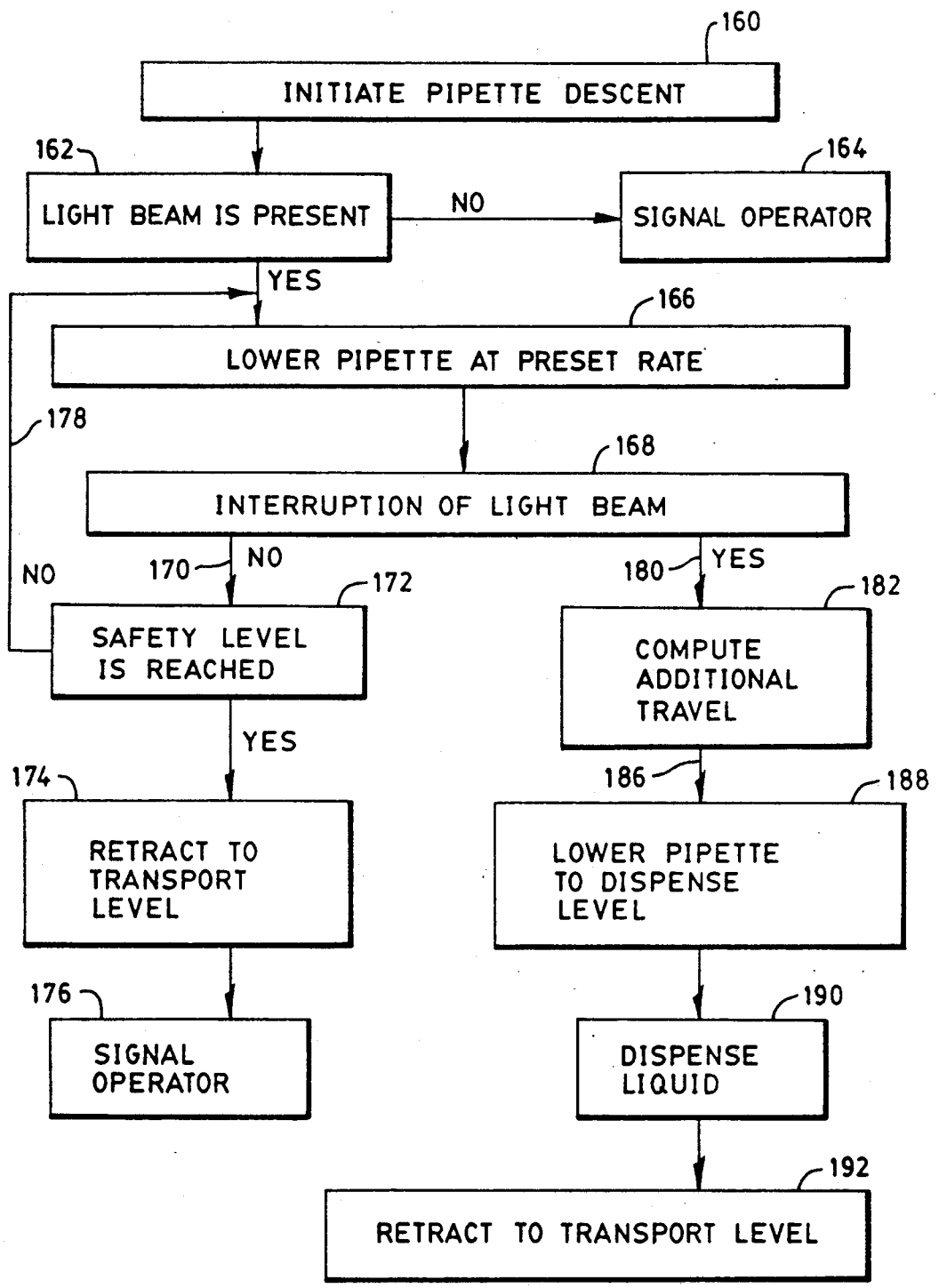
FIG. 5 is a flow chart showing operation of the microprocessor.

With reference to FIG. 5, the inventive feature of lowering the pipette to the cartridge 22 while compensating for variations in positions of the tip 70 is explained with reference to a flow chart. The flow chart describes operation of the microprocessor 62 of FIG. 2 for operating the vertical pipette drive 78 (FIGS. 2 and 4) for lowering the pipette 40 to dispense liquid reagent in a compartment 106 of the cartridge 22. Initiation of the pipette descent toward the cartridge 22 occurs at block 160. At block 162, the determination is made as to whether the light beam 114 (FIG. 2) is present. The microprocessor 62 is informed as to the status of the light beam by the signal outputted by the comparison circuitry 118. When the pipette 40 is in an elevated position, there is no blockage of the light beam 114 and, accordingly, the light beam 114 should be present and the comparator 120 should be outputting the logic-1 signal indicating full intensity of the light beam 114. If the beam is not present, then, at block 164, a person operating the test system 20 is signaled to correct an apparent fault in the equipment of the system 20.

If the light beam is present, the procedure advances to block 166 wherein the microprocessor 62 directs the lowering of the pipette 40 in the manner described above with reference to FIG. 4. Therein, the microprocessor 62 continually inputs new positions along the path of travel of the pipette 40 at a rate commensurate with the dynamic response of the feedback loop 142. Periodically, during the lowering of the pipette 40, the microprocessor 62 observes output signals of the comparison circuitry 118 to determine whether there has been an interruption of the light beam 114, this determination being performed at block 168.

Assuming that no interruption of the light beam 114 by the pipette 40 has occurred, then operation proceeds along line 170 to block 172 to determine whether the safety level (shown in FIG. 7), has been reached. There is the possibility of a system malfunction wherein the stem 72 of the pipette 40 has failed to secure the tip 70 at the table 68. This could occur for a variety of reasons, such as operator negligence in filling the table 68 with the set of tips 70, or the possibility of a cracked tip which fails to provide adequate friction for securing the tip to the stem 72. Since the shaft angle encoder 152 (FIG. 4) continually outputs position data to the microprocessor 62, the microprocessor 62 has knowledge of the location of the distal end of the stem 72. As the distal end of the stem 72 approaches the vicinity of the light beam 114, there should be an interruption of the beam 114 by the tip 70, assuming the tip 70 is present. The safety level is the lowest point at which the microprocessor 62 will allow the stem 72 to drop without interruption of the beam 114. If the safety level is reached, then the microprocessor 62 concludes that the tip 70 is absent, and operation proceeds to block 174 wherein the microprocessor 62 orders retraction of the pipette 40 to the transport level. As noted hereinabove, at the transport level, the pipette 40 clears the top wall 104 of the incubator 36 so that the stem 72 is fully visible to an operator for performing remedial action. From block 174, operation proceeds to block 176 wherein the operator is signaled to take remedial action.

During normal operation of the system 20, the tip 70 is present on the stem 72 and, accordingly, at block 172 the safety level would not be reached without interruption of the light beam 114. Accordingly, operation proceeds from block 172 along line 178 back to block 166 wherein the microprocessor 62 continues to lower the pipette at the preset rate. The operation continues in repetitive fashion through the blocks 166, 168, and 170 until interruption of the light beam 114 occurs at line 180. The interruption of the light beam 114 is signaled to the microprocessor 62 by a change in the output signal of the comparison circuitry 118 such that the signal changes from logic-1 to logic-0.

Assuming that the tip 70 is present, then, upon the interruption of the light beam at line 180, the output signal of the comparison circuitry 118 is at logic-0 to indicate to the microprocessor 62 that the tip 70 is filled with the liquid reagent, and that the tip 70 has reached the position of the light beam 114 along the path of travel of the tip 70 towards the cartridge 22. Accordingly, at block 182, the microprocessor 62 determines the position of the dispense level (FIG. 7) so as to compute the additional amount of travel required by the tip 70 to reach the dispense level. The operation within block 182 will be described in further detail with reference to FIG. 6.

In FIG. 5, the operation proceeds from block 182 via line 186 to block 188 wherein the pipette 40 is lowered further to locate the tip 70 at the dispense level. This lowering of the pipette is accomplished, in the manner disclosed hereinabove with reference to the feedback circuit 142 of FIG. 4, wherein the microprocessor 62 inputs further locations along the travel path of the pipette to bring the tip 70 to the dispense level. Thereafter, at block 190 the microprocessor 62 commands the suction control unit 128 to dispense liquid to the selected compartment 106 of the cartridge 22. Then at block 192, the pipette 40 is retracted back from the cartridge 22 to the transport level. The system 20 can now initiate other steps in the testing procedures of the samples carried by various ones of the cartridges 22.

FIG. 6 shows details in the procedure of block 182 (FIG. 5) for checking the filling of the pipette tip followed by the computation of the additional travel of the pipette. The procedure at line 180 proceeds to block 194 to check the intensity of the light beam. In the event that, at block 194, the light is fully obscured, the signal of the comparison circuit 118 is at logic-0, as was noted hereinabove, which allows the microprocessor 62 to determine, at block 198, that a loaded pipette is present. Thereupon, at block 200 the microprocessor reads the present pipette position as outputted by the encoder 152 (FIG. 4). This is followed, at block 202, by a reading of the position data of the cartridge 22, which data has been stored in the memory 154 (FIG. 4).

The cartridge position data designates the location of a top surface of the cartridge 22 relative to the top surface 158 of the carousel 24. Since the distance between the light beam 114 and the carousel surface 158 is known and fixed, the inputting of this cartridge data is equivalent to giving the microprocessor the distance between the top surface of the cartridge 22 and the beam 114. Accordingly, at block 204, the additional distance between the beam 114 and the cartridge 22 is added to the vertical distance already traveled by the pipette 40, the vertical distance being provided by the encoder 152. This gives the reading of the encoder 152 which will be obtained when the pipette tip 70 reaches the dispense level. This information is used by the microprocessor 62 in operating the circuit of FIG. 4 for continued lowering of the pipette 40. Accordingly, the operation can now proceed via line 186 to block 188 as has been disclosed above with reference to FIG. 5.

The timing diagram of FIG. 7 has already been referred to in the description of the circuitry of FIG. 4 and the procedure of FIGS. 5 and 6. Briefly, the diagram of FIG. 7 shows the descent of the pipette tip 70 at a fixed rate during the initial descent interval. This is followed by a pause in which the condition of the light beam is observed, followed by the final descent in which the pipette tip 70 is brought to the dispense level. At the conclusion of the dispense interval, the tip 70 is retracted to the transport level. The safety level is disposed between the light beam level and the dispense level.

The foregoing description provides for operation of the test system 20 in a fashion which allows the pipette to be lowered with an accuracy which is independent of the position of the pipette tip 70 on the pipette stem 72.

Figure 8:
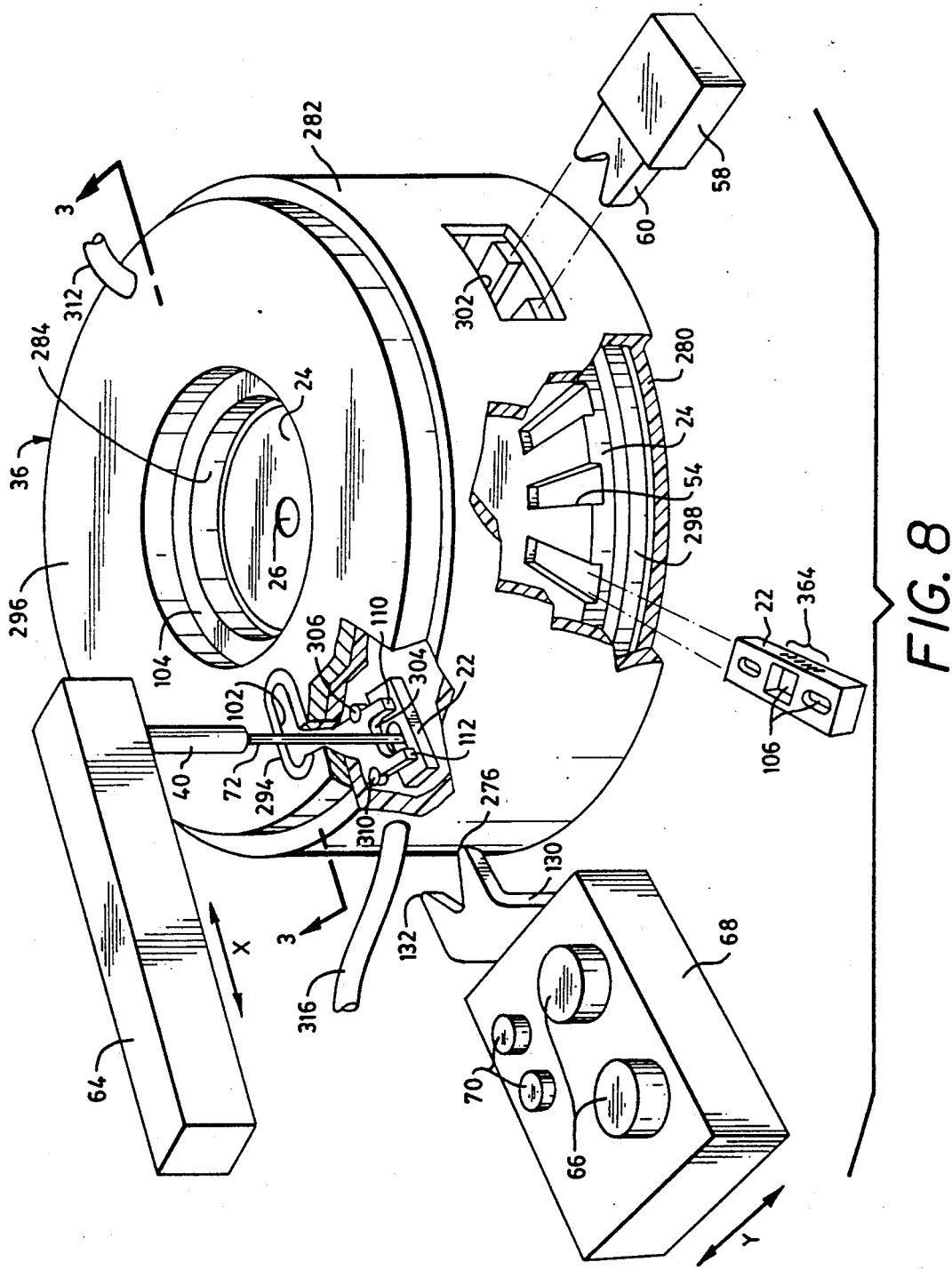
FIG. 8 is a further view of the test system of FIG. 1 with portions of the system indicated diagrammatically, FIG. 8 including a perspective view of an incubator with portions shown cut away to disclose interior components of the incubator.
Figure 9:
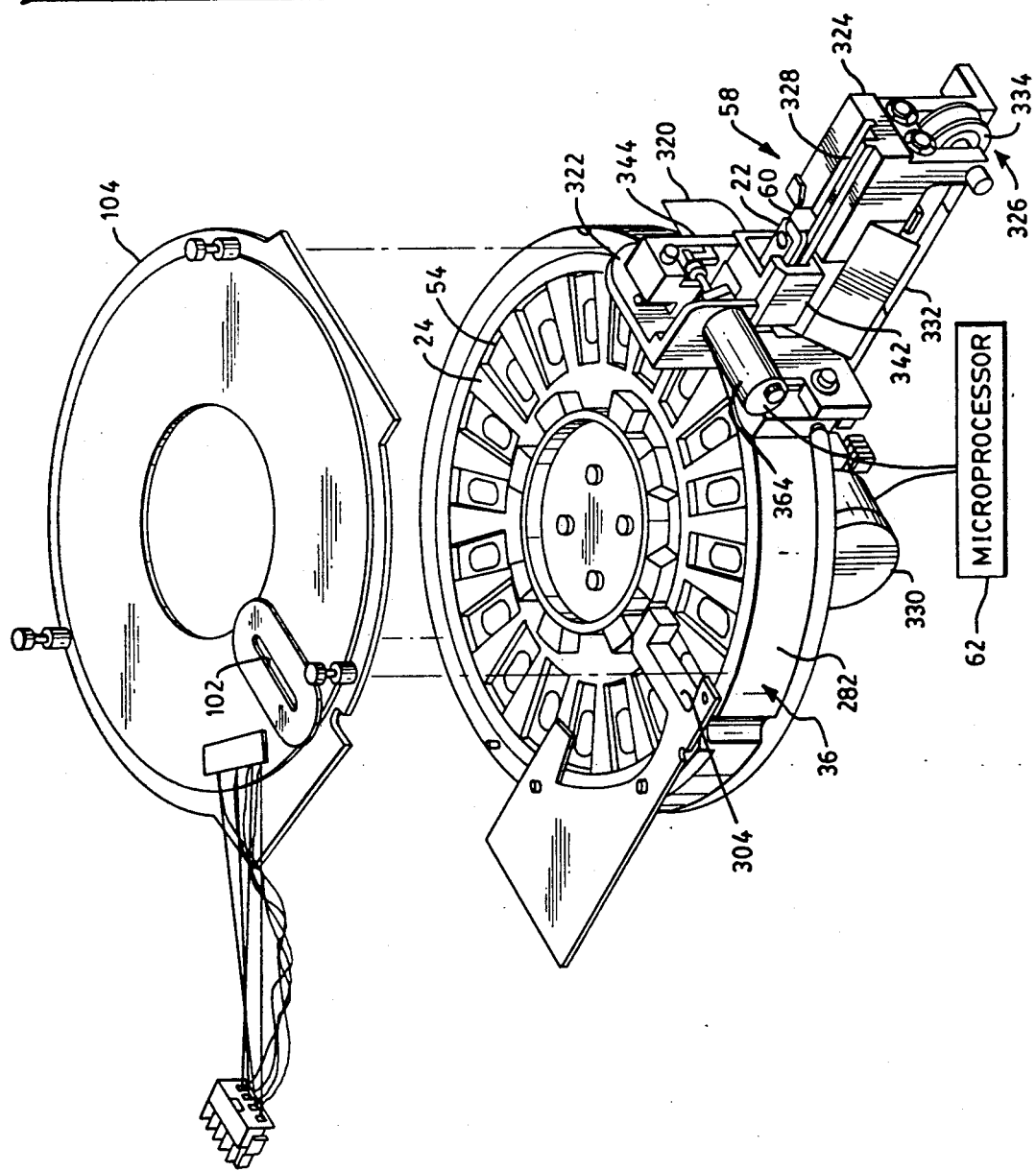
FIG. 9 is an exploded view of apparatus of an automated assay system showing a carousel disposed within a temperature-controlled chamber and an injector for inserting and extracting cartridges from berths in the carousel.
Figure 10:
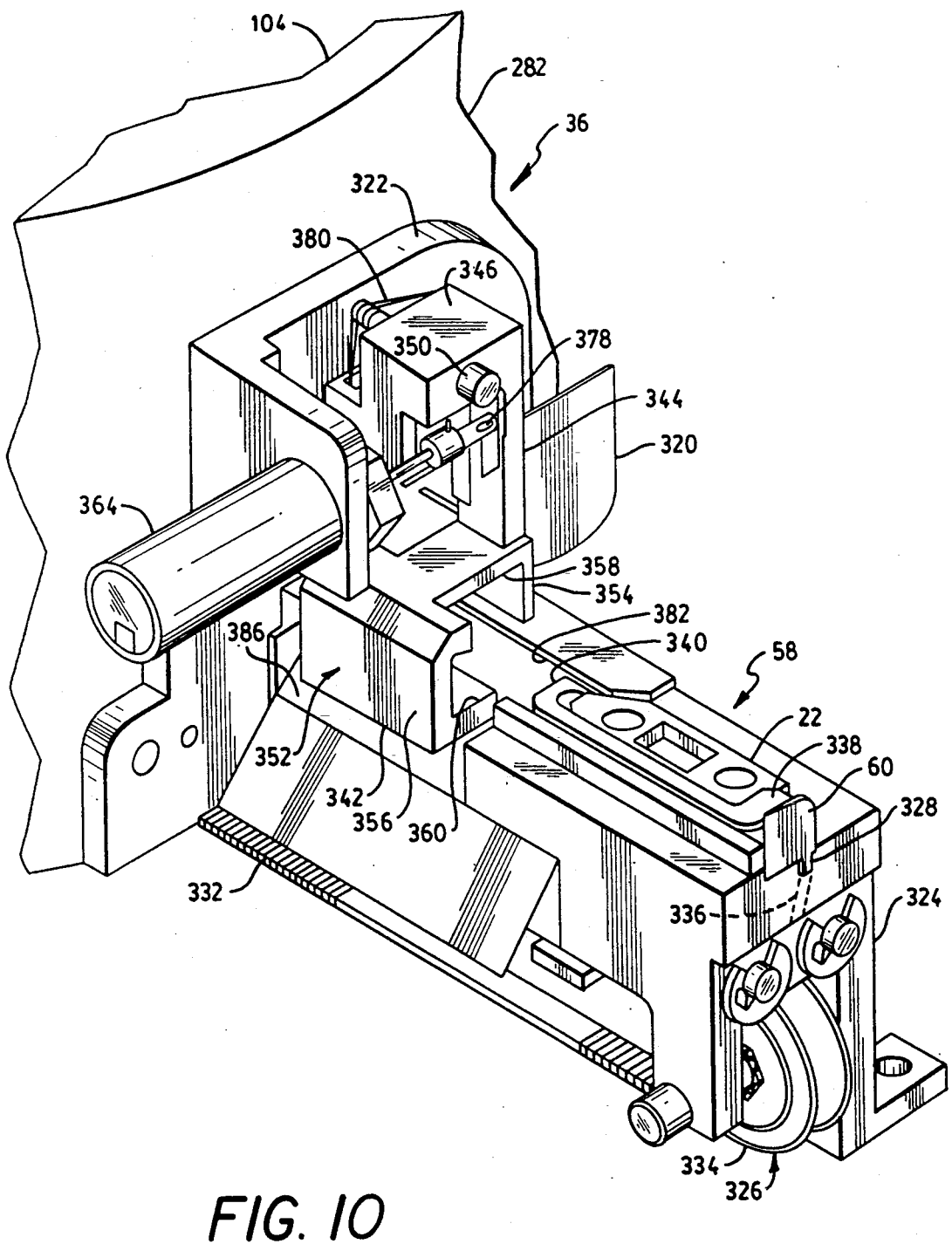

With reference to FIGS. 1, 8 and 9, there is provided further details in the construction of a preferred embodiment of the incubator 36 and its operation with the system 20. In addition to the top wall which serves as the roof 104 of the incubator 36 and is located above the carousel 24, the incubator 36 further comprises a bottom wall which serves as a floor 280 of the incubator 36 and is located below the carousel 24, and two sidewalls wherein one of the sidewalls is an outer wall 282 which extends from the roof 104 to the floor 280 and the second of the sidewalls is an inner wall 284 which extends from the roof 104 toward a central portion of the carousel 24. The roof 104 has an annular shape. An upper region 286 of the incubator 36 is bounded by the roof 104, the top surface 158 of the carousel 24, the outer wall 282 and the inner wall 284. The upper region 286 of the incubator 36 has a toroidal shape. The slot 102 in the roof 104 is relatively narrow, and is surrounded by a grommet 294. The slot 102 has a width large enough to clear the stem 72 and the tip 70 mounted on the distal end of the stem 72.

The incubator 36 further comprises two heaters, namely, a top heater 296 supported by the roof 104, and a bottom heater 298 supported by the floor 280 for controlling the incubator temperature. The bottom heater 298 is located in a lower region 300 of the incubator 36, between the carousel 24 and the floor 280. An injection port 302 is provided in the outer wall 282 facing the injector 58 to provide access to the loader arm 60 for inserting a cartridge 22 in a berth 54 of the carousel 24, and for extracting the cartridge 22 from the berth 54. A frame 304 is located within the upper region 286 for supporting sensors useful in the operation of the system 20, one such sensor 306 being provided for sensing the incubator temperature. The frame 304 is secured by a bracket 308 to the outer wall 282. By way of example in the construction of the frame 304, the frame 304 may be constructed as a circuit board for supporting electronic circuitry (not shown) such as a preamplifier for amplifying electrical signals provided by the sensor 306. By way of further example, an additional sensor 310 may also be mounted on the frame 304 for sensing the humidity because there are tests in which the humidity affects the outcome of the test, and a knowledge of the humidity can provide a more accurate reading of the test. Electrical cables 312, 314, and 316 connect respectively with the top heater 296, the bottom heater 298, and the sensors 306 and 310 for connecting these components to circuitry outside of the incubator 36.

In accordance with the invention, the injector 58 is provided with a door or shutter 320 (shown in FIGS. 9-13) for closing, or blocking, the injection port 302 (FIG. 8) in the outer wall 282 of the incubator 36. In accordance with a major feature of the invention, operation of the door 320 is performed automatically and in synchronism with the operation of the injector 58 during performance of the functions of insertion of a cartridge 22 into the incubator 36, extraction of a cartridge 22 from the incubator 36, and ejection of a spent cartridge, namely a cartridge for which the test procedure has been completed. In particular, the mechanism for positioning the door 320, as will be described in further detail hereinafter, moves the door 320 away from the port 302 for opening the port 302 prior to cartridge insertion and also prior to cartridge extraction. The door 320 is moved back in front of the port 302 to close the port 302 subsequent to the insertion of a cartridge and also subsequent to the extraction of a cartridge. These aspects of the invention are explained in the ensuing detailed description of the ejector 58.

With reference to FIGS. 9-13, the injector 58 includes a frame 322 for securing the injector 58 to the outer sidewall 282 of the incubator 36. A housing 324 extends radially outward from the frame 322 and supports a loader mechanism 326 including the loader arm 60 which engages with a cartridge 22 for advancing the cartridge 22 along a track 328 in the top side of the housing 324. The track 328 guides the cartridge 22 along a path through the port 302 into the incubator 36 for depositing the cartridge 22 in a berth 54 of the carousel 24.

Figure 11:
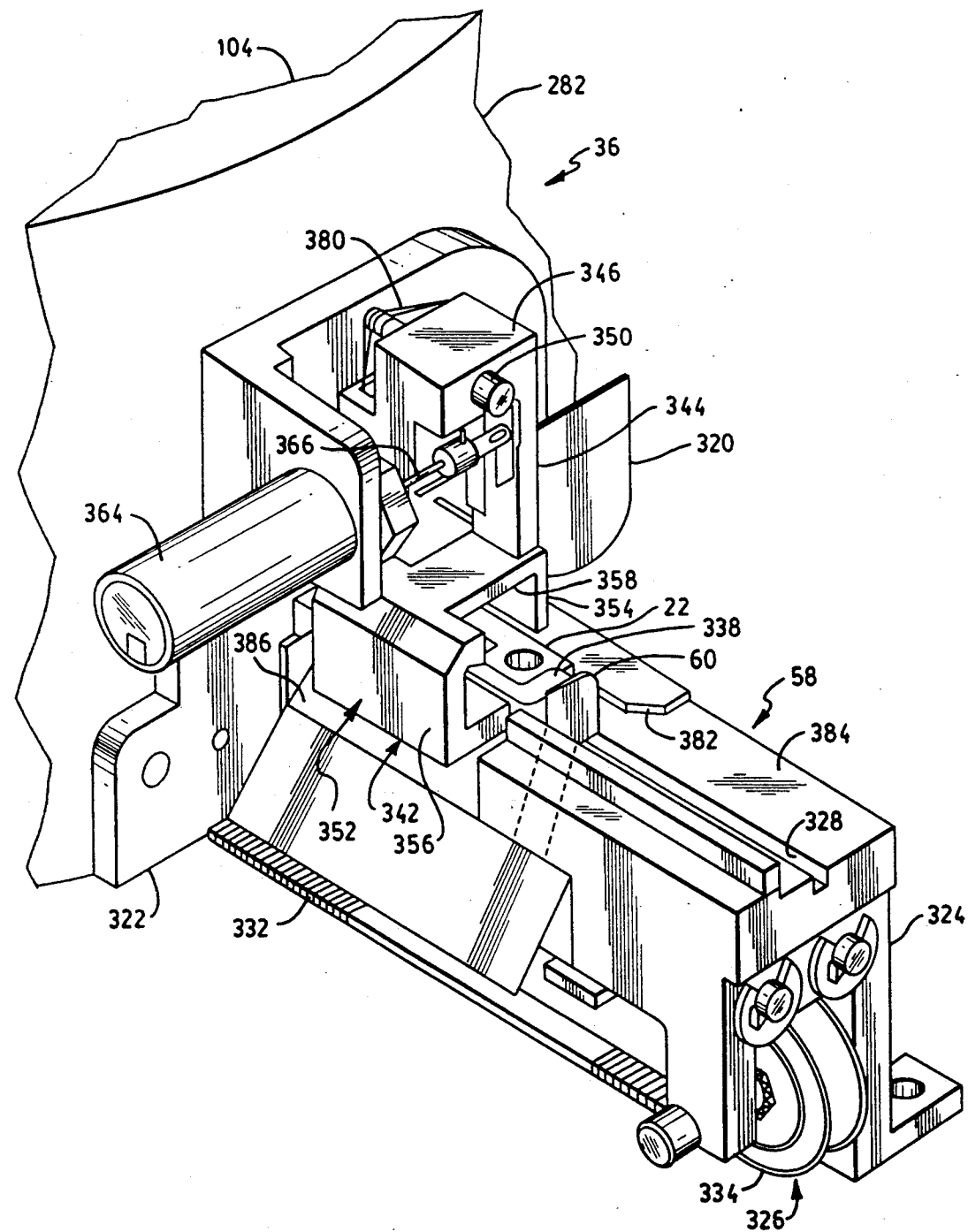

The loader mechanism 326 includes a stepping motor 330 (FIG. 9) which drives a belt 332 around a pulley 334 for connecting with the loader arm 60 via a projection 336 (shown in phantom in FIGS. 10 and 11) which extends downwardly from the loader arm 60. By virtue of the connection of the loader arm 60 with the belt 332, rotation of the stepping motor 330 in one direction advances the arm 60 towards the incubator 36 while rotation of the motor 330 in the reverse direction retracts the arm 60 from the incubator 36. The motor 330 is operated in response to signals from the microprocessor 62 in the same fashion as has been described hereinabove for the motors 28, 100, 90, and 86. The arm 60 extends in the longitudinal direction along the track 328 and curves in its end portions via two fingers 338 and 340 (FIG. 10) for receiving the cartridge 22. The cartridge 22 is inserted manually into the right side of the loader arm 60 as viewed in FIG. 10. During transfer of the cartridge 22 from the arm 60 to a berth 54, the cartridge 22 is disengaged from the arm 60 by rotating the carousel 24 momentarily in the counterclockwise direction. Conversely, during the extraction process, the cartridge 22 is placed in engagement with the arm 60 by rotating the carousel 24 momentarily in the clockwise direction. Upon extraction of the cartridge 22 from the incubator 36, the loader mechanism 326 places the loader arm 60 with the cartridge 22 at the eject position, as shown in FIG. 11. Thereupon, the cartridge 22 is disengaged from the loader arm 60 by operation of an ejector 342 as is explained in the ensuing description.

The ejector 342 comprises a leg 344 extending in a generally vertical direction and terminating in a transverse strut 346 at the top of the leg 344. The strut 346 has a horizontal bore 348 for receiving a pivot 350 extending outwardly from the frame 322 so as to accomplish a pivoting of the ejector 342 about the pivot 350. The ejector 342 further comprises a guide 352 disposed at the opposite end of the leg 344 and integrally formed therewith. The guide 352 includes an inner sidewall 354 extending parallel to the leg 344, and an outer sidewall 356 spaced apart from the inner sidewall 354 and parallel thereto. The guide 352 further comprises an arm 358 which extends generally horizontally and connects the top of the inner sidewall 354 with the top of the outer sidewall 356. A bottom of the outer sidewall 356 is formed as a portion 360 of track and extends in a plane, parallel to the arm 358, towards the bottom edge of the inner sidewall 354. The track portion 360 includes a lip 362 for engagement with the cartridge 22 upon passage of the cartridge 22 through the ejector 342. The ejector 342 is shown in a vertical orientation in FIG. 13 and in an inclined orientation in FIG. 12, the inclined orientation of FIG. 12 occurring by virtue of a pivoting about the pivot 350. The leg 344 in combination with the arm 358 and the outer sidewall 356 constitute a swing arm by which the track portion is swung into and out of the travel path of the cartridge 22.

Figure 12:
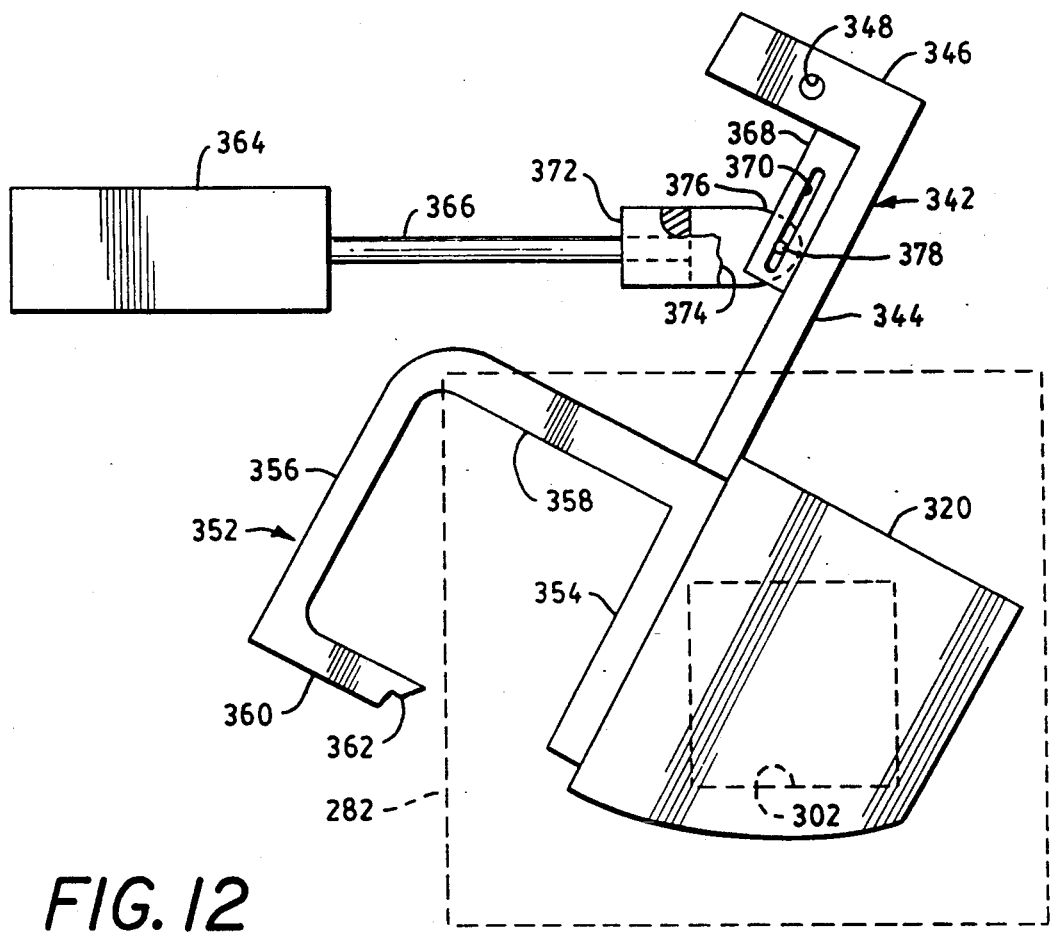
FIG. 12 is a stylized view showing a door and ejector assembly of FIG. 10 with a sidewall of the temperature-controlled chamber being shown in phantom, the door being positioned to close a cartridge port of the chamber.

In accordance with the invention, the door 320 is secured to an end of the inner sidewall 354 facing the outer wall 282 of the incubator 36. Thereby, the door 320 becomes an integral part of the structure of the ejector 342 to move concurrently with movements of the guide 352, and to swing via the swing arm about the pivot 350. The door 320 has a planar form and is disposed with its planar surface facing the wall 282 of the incubator 36. The door 320 is virtually contiguous to the wall 282, but is separated from the wall 282 by a clearance gap (not shown) so as to facilitate relative motion between the door 320 and the wall 282. In the situation of the inclined orientation of the ejector 342, as depicted in FIG. 12, the door 320 acts as a closure element of the cartridge ejection port 302 in the wall 282. In the case of the vertical orientation of the ejector 342, as depicted in FIG. 13, the door 322 is positioned off to the side of the port 302 so as to open the port 302 to allow passage of the cartridge 22 via the port 302.

Pivoting of the ejector 342 is accomplished by means of an electrically actuated solenoid 364 having a rod 366 extending therefrom in a transverse direction towards a slotted member 368 of the ejector 342, the member 368 being disposed on the leg 344 at a location directly beneath the strut 346. The member 368 has an elongated slot 370 extending in a direction parallel to the leg 344. A bifurcated element 372 is mounted on an end of the rod 366 opposite the solenoid 364 and includes a pair of fingers 374 and 376 which pass along opposite sides of the member 368 and support a pin 378 which extends through the slot 370. Activation of the solenoid 364 pushes the rod 366 against the force of a spring 380 to accomplish a rotation or pivoting of the ejector 342 in the counterclockwise direction so as to place the ejector 342 in the attitude shown in FIG. 13. Deactivation of the solenoid 364 allows the spring 380 to urge the ejector 342 to rotate or pivot in the clockwise direction to attain the attitude shown in FIG. 12. The solenoid 364 is activated by signals from the microprocessor 62, and is operated by the microprocessor 62 in synchronism with the motors 330 and 28 so as to drive the door 320 in the appropriate directions for opening and closing the port 302 in conjunction with the cartridge insertion and cartridge extraction operations of the injector 58.

Figure 13:
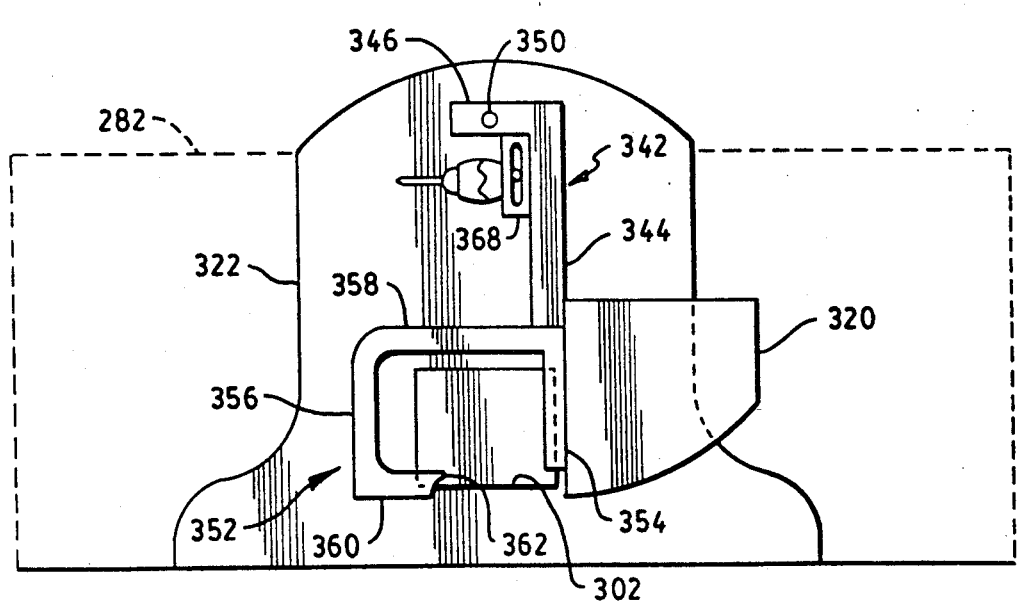
FIG. 13 is a simplified view of the ejector of FIG. 10 with the door and ejector assembly shown in a position wherein the cartridge port is open.

The track portion 360 serves as an extension of the track 328 when the ejector 342 is in the vertical attitude of FIG. 13. In this condition of the ejector 342, the cartridge 22 rides upon the track 328 and also upon the lip 362, the cartridge being held against the lip 362 by an abutment 382 disposed on a floor 384 of the track 328. The floor 384 forms a top surface of the housing 324. The floor 384 also holds the cartridge 22 in the load position, shown in FIG. 10, the floor 384 receding in the vicinity of the ejector 342 to change into a discharge chute 386. The receding of the floor 384 in the vicinity of the ejector 342 allows the cartridge 22 to ride upon the abutment 382 and upon the lip 362. Upon a pivoting of the lip 362 away from the abutment 382, the cartridge 22 falls beneath the loader arm 60 into the chute 386, and slides away to a bin (not shown) for collection of spent cartridges. During the pivoting of the lip 362 away from the abutment 382, the inner sidewall 354 comes into contact with the cartridge 22 to push the cartridge 22 down the chute 386.

Thereby, the invention has attained the objective of providing a door for the cartridge injection port and, furthermore, has provided the feature of combining movement of the door with movement of the ejector. Thereby, better temperature control of the incubator is attained essentially without adding complexity to the structure of the injector.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. An automated assay system for use with assay cartridges, the system comprising
    a temperature controlled chamber, the chamber having a top wall and a bottom wall and a sidewall connecting the top wall with the bottom wall, the sidewall encircling the chamber, there being a port in the sidewall and a door for closing the port;
    a plurality of berths disposed in the chamber for receiving cartridges;
    a conveyor disposed in the chamber for conveying said berths along the sidewall and sequentially past said port;
    an injector disposed outside said chamber and at said port for inserting a cartridge via said port into one of said berths and for extracting a cartridge via said port from one of said berths; and
    wherein said injector includes means for opening the door prior to cartridge insertion or cartridge extraction and for closing the door subsequent to a cartridge insertion or a cartridge extraction and means for ejecting a spent cartridge subsequent to extraction of the cartridge from said chamber
    said injector including a track for guiding a cartridge along a path into said chamber, a portion of said track being included in said ejecting means, wherein said track portion is arranged to swing away from said path during ejection of a cartridge to dislodge a cartridge from the path to accomplish ejection of the cartridge.

2. A system according to claim 1 wherein
    said ejecting means further comprises a pivot and a swing arm connecting said pivot to said track protion, said swing arm supporting said track portion during a swinging of said track portion;
    said door is secured to said swing arm to swing concurrently with a swinging of said track portion;
    a swinging of said track portion by said swing arm away from said path brings said door into a position of closure of said port, and a returning of said track portion to said path by said swing arm advances said door to open said port.

3. A system according to claim 1 wherein said injector further comprises:
    a loader arm for engaging with a cartridge to advance the cartridge along said path;
    first drive means for pivoting said swing arm;
    second drive means for moving said loader arm along said path; and
    wherein said system further comprises means for synchronizing operation of said first and said second drive means for opening said port prior to insertion or extraction of a cartridge.

4. A system according to claim 3 wherein
    said first drive means comprises a solenoid;
    said second drive means comprises a stepping motor; and
    said synchronizing means is operatively coupled to said conveyor to position a berth at said port during cartridge insertion or cartridge extraction, the conveyor being a rotatable carousel.

* * * * *